(12) United States Patent
Alexandre

(10) Patent No.: US 8,197,440 B2
(45) Date of Patent: Jun. 12, 2012

(54) NEEDLELESS INJECTION DEVICE WITH DOUBLE STOPPER WITH LOW PRESSURE PROFILES

(75) Inventor: Patrick Alexandre, Gray (FR)

(73) Assignee: Crossject (FR)

( * ) Notice: Subject to any disclaimer, the term of this patent is extended or adjusted under 35 U.S.C. 154(b) by 346 days.

(21) Appl. No.: 12/374,514

(22) PCT Filed: Jun. 26, 2007

(86) PCT No.: PCT/FR2007/001055
§ 371 (c)(1),
(2), (4) Date: Jan. 21, 2009

(87) PCT Pub. No.: WO2008/009786
PCT Pub. Date: Jan. 24, 2008

(65) Prior Publication Data
US 2009/0326446 A1    Dec. 31, 2009

(30) Foreign Application Priority Data

Jul. 18, 2006   (FR) ...................................... 06 06506

(51) Int. Cl.
*A61M 5/30* (2006.01)
(52) U.S. Cl. .......................................... 604/69; 604/140
(58) Field of Classification Search .............. 604/68–70, 604/140–141, 143
See application file for complete search history.

(56) References Cited

U.S. PATENT DOCUMENTS
2002/0151842 A1*  10/2002  Gonnelli et al. ................ 604/70

FOREIGN PATENT DOCUMENTS
| FR | 2 853 836 | 10/2004 |
| FR | 2 865 407 | 7/2005 |
| WO | 01/58512 | 8/2001 |

OTHER PUBLICATIONS
International Search Report; PCT/FR2007/001055; Oct. 15, 2007.

* cited by examiner

*Primary Examiner* — Laura A Bouchelle
*Assistant Examiner* — Melissa A Snyder
(74) *Attorney, Agent, or Firm* — Cantor Colburn LLP

(57) ABSTRACT

The present invention relates to a needleless injection device (1) comprising a reservoir (3), obturated by an upstream stopper (4) and a downstream stopper (5) between which a liquid active principle (6) is accommodated, and a receptacle (7) comprising at least one injection conduit (8), said receptacle comprising a cavity (10) whose height is equal to the distance traveled by the downstream stopper before each injection conduit is opened, —the height of the cavity in millimeters being between a minimum height and a maximum height, respectively defined by the following relationships, •minimum height=3, •maximum height=15×exp. ($-(V/9)^2$)+10, where V is the initial speed of ascent of the pressure profile expressed in bar per microsecond, —the ratio between the length of each injection conduit and the height of the cavity being between 1 and 2.

17 Claims, 3 Drawing Sheets

NEEDLELESS INJECTION DEVICE WITH DOUBLE STOPPER WITH LOW PRESSURE PROFILES

TECHNICAL FIELD OF THE INVENTION

The technical field of the invention is that of prefilled, disposable needleless injection devices, operating with an energy source such as, for example, a gas generator and used for intradermal, subcutaneous and intramuscular injections of a liquid active principle for therapeutic use in human or veterinary medicine.

The active principle consists of a more or less viscous liquid, a liquid mix, or a gel. The active principle may also be a solid in solution in a solvent suitable for injection, or consist of a powdery solid suspended at a certain concentration in an appropriate liquid. The particle size of the active principle must therefore be compatible with the diameter of the ducts to avoid blocking them.

BACKGROUND OF THE INVENTION

As used in the present application, the term 'liquid active principle' constitutes the generic definition covering all the previously mentioned embodiments of the active principle.

Needleless injection devices comprising a reservoir of liquid active principle already exist in tube form and have been the subject of patents. For example, the patent application FR 2 853 837 may be cited, which relates to a needleless injection device comprising an injection nozzle and a tube intended to receive a liquid active principle to be injected, said tube being fixed to said nozzle with the help of connecting means.

The person skilled in the art traditionally seeks to minimize or even eliminate the risks of damaging, on the one hand, the tube containing the liquid active principle and, on the other hand, the downstream stopper in the specific 'double stopper' configuration described, in particular, in the patent application WO 01/58512. Said configuration is characterized by the presence of a column of liquid delimited, on the one hand, by the side wall of the tube and, on the other hand, by an upstream stopper and a downstream stopper, between which the liquid active principle is housed. Under the effect of the gas generation, said column moves in the tube until the downstream stopper comes into contact with the base of a receptacle located in the nozzle so as to free the injection ducts in order to expel said active principle. However, when the downstream stopper hits the base of said receptacle, it creates a shockwave that will propagate through to the tube and the intensity of which is a maximum at the end of said tube which is in contact with the nozzle. In a 'double stopper' configuration, the downstream stopper and the glass tube are the two most stressed elements during the operation of the needleless injection device. The latter must consequently be shaped in such a way that the speed of impact of the downstream stopper in the receptacle is less than the limit speed acceptable for the mechanical strength of the components of said injection device. In addition, it is known that the time separating the opening of the injection ducts and the start of the output of the jet from the injection ducts must be longer than the attenuation time of the pressure oscillations generated by the opening of the injection ducts.

In the technical literature of the field in question it is traditionally mentioned that it is necessary to apply, to the liquid active principle to be injected, on the one hand a high pressure between 200 and 500 bar in order to pierce the skin, and on the other hand a constant or decreasing pressure through to the end of the injection in order to ensure the transfer of the liquid active principle, the final values generally being between 40 and 250 bar.

However, there is a major stake in reducing the operating pressures so as to construct strong and economical needleless injection devices, more particularly for single-use devices or the consumable parts, such as the injection nozzle, of reusable devices while guaranteeing good reproducibility of injections.

SUMMARY OF THE INVENTION

It has been surprisingly observed that the subject of the present invention precisely enables excellent needleless injection results to be attained with pressure profiles with initial values between 50 and 150 bar, preferably between 70 and 100 bar, i.e. values clearly lower than those commonly accepted in the field considered.

More precisely, the subject of the present invention relates to a needleless injection device comprising an energy source such as a gas generator, a reservoir blocked by an upstream stopper and a downstream stopper between which a liquid active principle is housed, and an injection nozzle equipped with a receptacle and with at least one injection duct, said receptacle containing a cavity with a height equal to the distance covered by the downstream stopper before opening each injection duct, characterized in that it is shaped such that:

the height of the cavity in millimeters is between a minimum height and a maximum height respectively defined by the following equations:

•minimum height=3

•maximum height=$15 \times \exp(-(V/9)^2)+10$ where V is the speed of the initial increase in the pressure profile expressed in bars per microsecond;

the ratio between the length of each injection duct and the height of the cavity is between 1 and 2.

The speed of the initial increase in pressure will be understood to involve the calculation of dP/dt throughout a period of time going schematically from 0 to 0.5 millisecond.

In addition, with a needleless injection device according to the invention it is possible to obtain pressure profiles that are not necessarily flat or uniformly decreasing, in contrast to what is commonly accepted today in the literature.

Even if several parameters such as the number and the diameter of the orifices in the injection ducts, or the quantity of liquid active principle, play a part in controlling the injection depth, a crucial advantage of the invention lies in the fact that the large variety of permitted shapes of pressure profile, depending on the type of energy source used, ensures fine and optimized management of the injection depth.

Moreover, another considerable advantage of a needleless injection device according to the invention is the fact that it has been observed that the final pressure has no influence on performance as long as it is greater than 20 bar, which should be compared with the final values of 40 to 250 bar commonly accepted in the literature.

Advantageously, the minimum height of the cavity in millimeters is defined by the following equation:

•minimum height=$12 \times \exp(-(V/18)^2)+4$.

Again advantageously, the maximum height of the cavity in millimeters is defined by the following equation:

•maximum height=$14 \times \exp(-(V/9)^2)+9$.

Preferably, the ratio of the length of each injection duct and the height of the cavity is between 1.1 and 1.6.

Again preferably, the needleless injection device according to the invention is shaped in such a way that the time for an increase in pressure to 80 bar is schematically between 0.2 and 2.0 milliseconds.

Advantageously, the energy source consists of a pyrotechnic gas generator equipped with a pyrotechnic charge and an ignition system.

BRIEF DESCRIPTION OF THE DRAWINGS

The invention will be better understood with the help of the detailed description set out below with regard to the appended drawing in which.

DETAILED DESCRIPTION OF THE PREFERRED EMBODIMENTS

Figure 1:
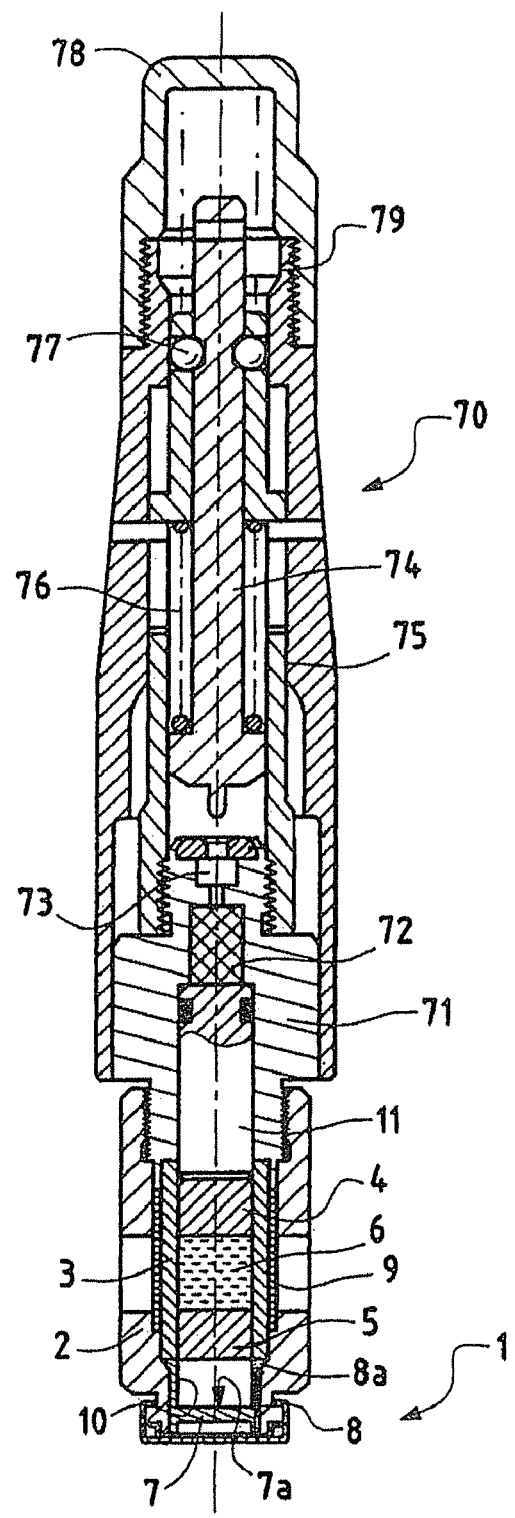
FIG. 1 is a schematic longitudinal cross section view of a needleless injection device according to the invention.

A needleless injection device 1 according to the invention, as generally shown in FIG. 1, comprises a body 2 in which a reservoir 3 containing a liquid active principle 6 is housed.

An injection nozzle comprising a receptacle 7 is positioned at the downstream end of the body 2, the injection system being conventionally covered by an outer protection (not shown) to ensure the asepsis of the injection device 1.

A pyrotechnic gas generator 70 containing a pyrotechnic charge 72 is fixed by being screwed to the upstream end of the body 2 by means of a connecting member 71 which bears on the reservoir 3, the seal being ensured by a circular O-ring.

The body 2 of the injection device 1 comprises two diametrically opposite windows in order to view the liquid active principle 6 contained in the reservoir 3. Downstream of the body 2, in a suitably shaped bore, the receptacle 7, which will be described in more detail below, is shrunk on. The reservoir 3 bears on the receptacle 7 and is centered in the downstream part of the body 2, an intermediate transparent material 9 being positioned around said reservoir 3. Upstream, the body 2 receives the connecting member 71 which is centered around the end of the reservoir 3. The latter essentially consists of a glass tube closed at both ends by a movable upstream stopper 4 and a movable downstream stopper 5, these being elements conventionally used in needleless injection devices and obtained by molding elastomers compatible with the liquid active principle 6 for a long duration, for example chlorobutyl or bromobutyl whose Shore hardness is schematically set between 45 and 70. These elements may receive surface treatments, in particular to facilitate their movement in the tubular reservoir 3. At rest, each element has a diameter about 10% greater than the internal diameter of the reservoir 3 and a height schematically between 0.5 and 0.8 times this diameter. Once engaged, each element has, due to the deformations it undergoes, a height of between around 0.6 and 1.0 times the internal diameter of the reservoir 3.

In this exemplary embodiment, the receptacle 7 is implemented by a part of cylindrical-conical outer shape which comprises a central cavity 10 in which the downstream stopper 5 will come to be housed. On its periphery the receptacle 7 comprises three injection ducts 8 uniformly offset in relation to each other. The diameter of the central cavity 10 is equal to that of the reservoir 3, and its free height is equal to that of the downstream stopper 5. When the latter has reached the base 7a of the receptacle 7 due to the actuation of the pyrotechnic gas generator 70, each injection duct 8 is then brought into communication with the liquid active principle 6 by means of an inlet 8a, said liquid active principle 6 flowing with a speed corresponding to the pressure transmitted by the upstream stopper 4.

More precisely, the height of the cavity 10 in millimeters is chosen so as to be between a minimum height and a maximum height respectively defined by the following equations:

- minimum height=3

- maximum height=$15 \times \exp(-(V/9)^2)+10$ where V is the speed of the initial increase in the pressure profile expressed in bars per microsecond. The speed of the initial increase in pressure will be understood to involve the calculation of dP/dt throughout a period of time going schematically from 0 to 0.5 millisecond. In addition, each injection duct 8 is shaped so that the ratio of the length of said injection duct 8 to the height of the cavity 10 is between 1 and 2.

According to a preferred embodiment, the height of the cavity 10 in millimeters is between a minimum height and a maximum height respectively defined by the following equations:

- minimum height=$12 \times \exp(-(V/18)^2)+4$

- maximum height=$14 \times \exp(-(V/9)^2)+9$ and the ratio of the length of each injection duct 8 to the height of the cavity 10 is between 1.1 and 1.6.

Even if several parameters such as the number and the diameter of the orifices in the injection ducts 8, or the quantity of liquid active principle 6, play a part in controlling the injection depth, it should be properly understood that a large variety of pressure profile shapes is available.

Figure 2:
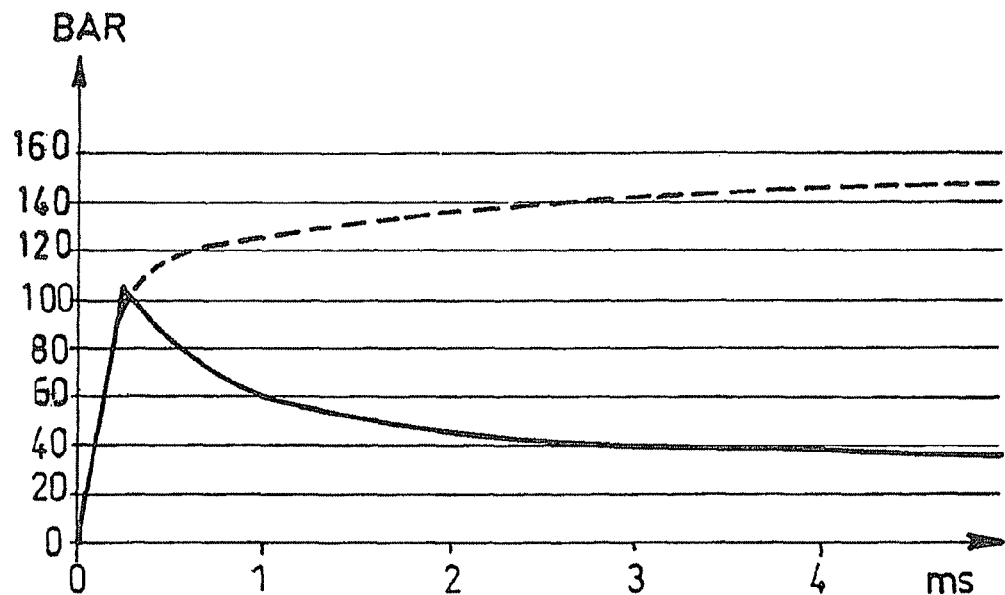
FIGS. 2 to 5 show examples of pressure profile curves obtained as a function of the velocity of the energy source used.
Figure 3:
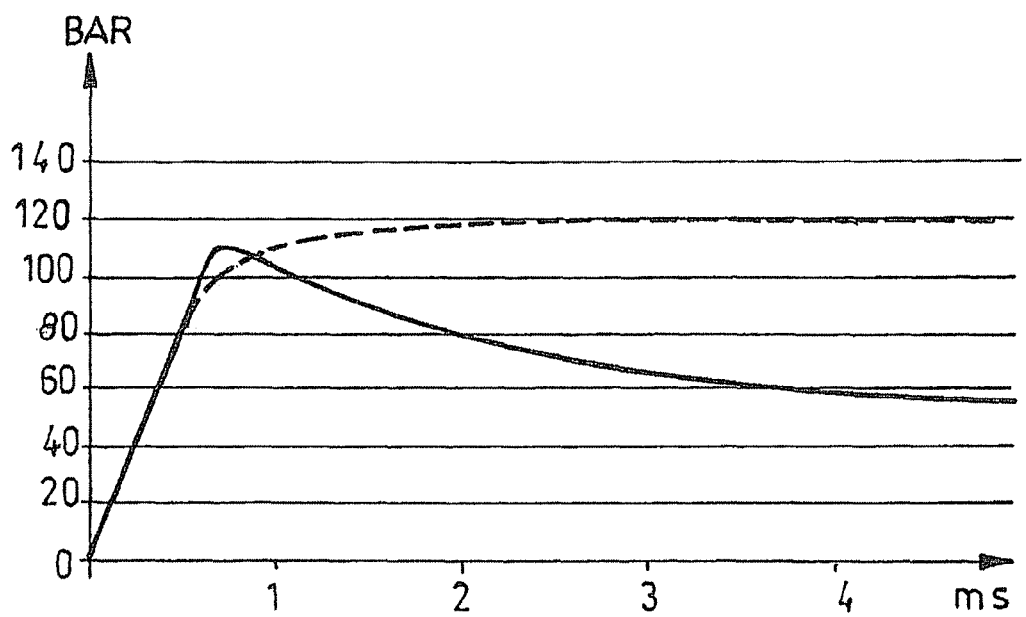
Figure 4:
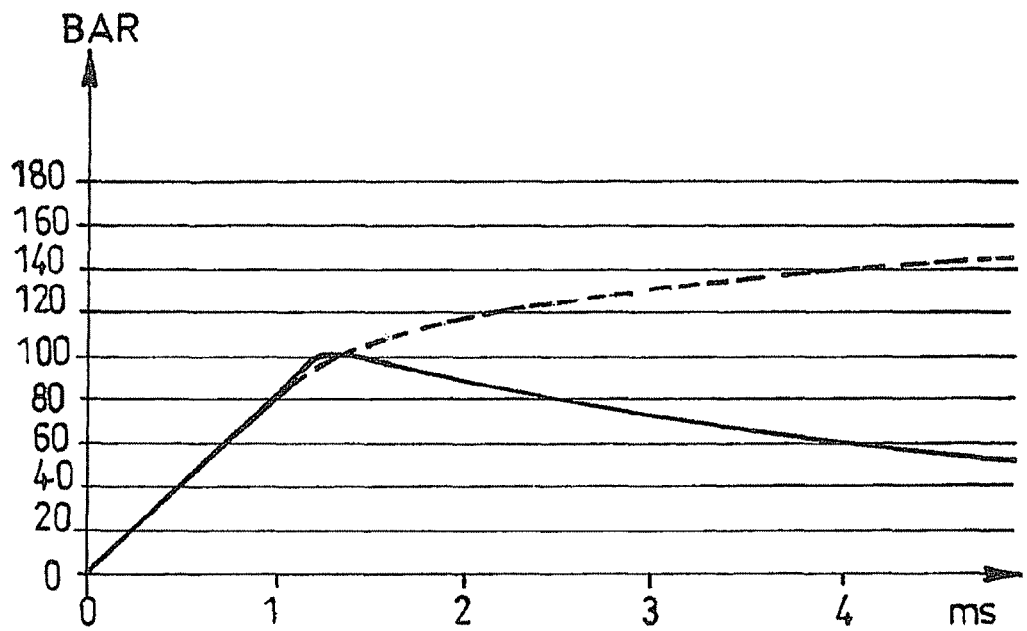
Figure 5:
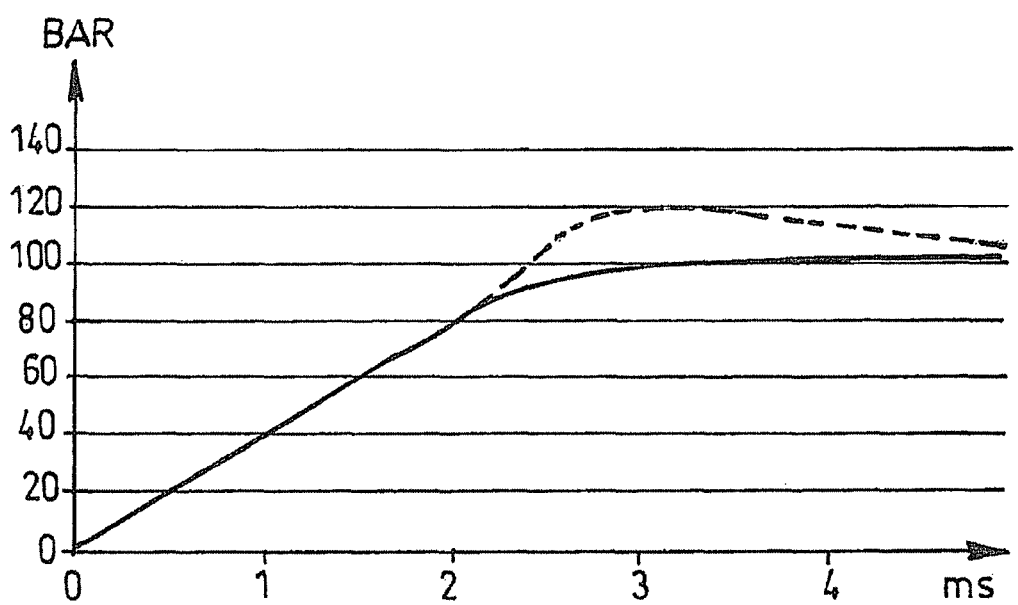

Indeed, with reference to FIGS. 2 to 5, it will be noticed that just as much for a pyrotechnic charge 72 of high intensity, the pressure profile of which is shown in FIG. 2 and characterized by a time for an increase in pressure to 80 bar of around 0.2 millisecond, as for other pyrotechnic charges 72 of medium, low, or very low intensity, the pressure profiles of which are shown in FIGS. 3 to 5 and which are characterized by a time for an increase in pressure to 80 bar of around 0.5 millisecond, 1.0 millisecond and 2.0 milliseconds respectively, it is possible to obtain different pressure profiles for a given intensity according to the type of primer 73 chosen to initiate the pyrotechnic charge 72. By way of illustration, in each of the configurations shown in FIGS. 2 to 5, two examples of different pressure profile curves are plotted. The preferred pressure profile curve with the lowest final pressure is shown with a continuous line and the pressure profile curve with the highest final pressure is shown with a dotted line.

It has been observed that it is possible, for example, to carry out completely satisfactory subcutaneous injections of 0.5 milliliter of liquid active principle 6 with a pressure of around 80 bar at the start of the injection and of 30 bar at the end of the injection, for an injection device 1 equipped with three injection ducts 8 of 250 micrometers diameter. Of course, the pressure values and the number/diameter of the injection ducts 8 are suited to the quantity of liquid active principle 6 to be injected, along with its viscosity and the desired injection depth.

In this embodiment the pyrotechnic gas generator 70 acts on the upstream stopper 4 by means of a piston 11 of effective cross section equal to that of said upstream stopper 4. Since this piston 11 is in contact with the upstream stopper 4, there is therefore no shock or ram effect at the start of operation. This piston 11, thanks to its sealing system, prevents the gases generated by the combustion of the pyrotechnic charge 72 from coming into contact with the upstream stopper 4, and therefore allows possible damage thereof and gas leakage into the liquid active principle 6 contained in the reservoir 3 to be avoided. The piston 11, of a suitable color, may also serve as an operating indicator by appearing in the viewing windows of the body 2.

At this stage we will generally describe the main elements of the pyrotechnic gas generator 70 on top of the pyrotechnic charge 72 and the primer 73. More precisely, the pyrotechnic gas generator 70 comprises a connecting member 71 positioned around the piston 11, and in which the pyrotechnic charge 72 is located, just above said piston 11. The primer 73 is mounted on top of the pyrotechnic charge 72, the combustion of which is initiated when said primer 73 is struck by a striker 74. In the initial position, the striker 74 is held in a striker guide 75 screwed into the connecting member 71 by balls 77 partly engaged in a groove in the striker 74. A striking device is also provided and breaks down into a pusher 78 having an enlarged groove 79 and an internal spring 76. The pusher 78 slides on the outside of the striker guide 75, and it is held by lugs moving in lateral grooves. This pusher 78 constitutes in this example the triggering element.

Of course, to initiate the combustion of the pyrotechnic charge 72, it is possible, without departing from the scope of the invention, to use initiation devices other than the previously described striker device. Without going into details and without seeking to be exhaustive, we mention as examples electric battery initiation devices or piezoelectric initiation devices.

The pyrotechnic gas generator 70 may optionally be replaced by a gas generator consisting of a reservoir of compressed gas closed by a quick opening valve. The triggering element will open said valve, and the compressed gases from the reservoir will then be able to expand and act on the pushing means.

For the use of the injection device 1 according to the invention, after having removed the asepsis cap and having placed the downstream side of said injection device 1 on the skin of the subject to be treated, the operator presses with his/her thumb the pusher 78, which is pushed in, compressing the spring 76. The pusher 78 moves translationally until the enlarged groove 79 of the striker 74 reaches the height of the balls 77. On doing this, the latter balls engage under the effect of gravity in the enlarged groove 79 and thus release the striker 74 which then violently strikes the primer 73, the initiation of which ignites the pyrotechnic charge 72. The gases generated by the latter will, in a known manner, force the column consisting of the upstream stopper 4, the liquid active principle 6 and the downstream stopper 5 to slide along the reservoir 3 until the downstream stopper 5 stops against the base 7a of the receptacle 7. Under the effect of the deformation, the downstream stopper 5 frees the inlets 8a of the injection ducts 8 and therefore allows the liquid active principle 6 to be injected at high speed so as to be able to pass through the skin of the person to be treated.

Although the invention has been described in connection with particular exemplary embodiments, it is obvious that it is in no way limited thereto and that it covers all the technical equivalents of the means described and their combinations if these fall within the scope of the invention.

The invention claimed is:

1. A needleless injection device comprising:
   an energy source adjacent a first end of the injection device;
   a reservoir blocked by a movable upstream stopper and a movable downstream stopper between which a liquid active principle is housed, said movable upstream stopper being disposed adjacent said first end; and
   an injection nozzle disposed adjacent said second end and further equipped with a receptacle and at least one injection duct, said receptacle containing a cavity with a height equal to a distance covered by the movable downstream stopper before opening each injection duct, wherein the needleless injection device is shaped such that:
   a height of the cavity in millimeters is between a minimum height and a maximum height respectively defined by the following equations:

•minimum height=3

•maximum height=$15 \times \exp(-(V/9)^2)+10$ where V is a speed of an initial increase in a pressure profile expressed in bars per microsecond;
   a ratio between a length of each injection duct and the height of the cavity is between 1 and 2.

2. The needleless injection device as claimed in claim 1, wherein the minimum height of the cavity in millimeters is defined by the following equation:

•minimum height=$12 \times \exp(-(V/18)^2)+4$.

3. The needleless injection device as claimed claim 1, wherein the maximum height of the cavity in millimeters is defined by the following equation:

•maximum height=$14 \times \exp(-(V/9)^2)+9$.

4. The needleless injection device as claimed in claim 1, wherein the ratio of the length of each injection duct and the height of the cavity is between 1.1 and 1.6.

5. The needleless injection device as claimed in claim 1, wherein the needleless injection device is shaped in such a way that a time for an increase in pressure to 80 bar is between 0.2 and 2.0 milliseconds.

6. The needleless injection device as claimed in claim 1, wherein the energy source consists of a pyrotechnic gas generator equipped with a pyrotechnic charge and an ignition system.

7. A needleless injection device comprising:
   a body having a first end and a second end, said first end adjacent an energy source connected thereto;
   a reservoir disposed within said body and containing a liquid active principle, said reservoir having first and second movable stoppers at opposite ends thereof, at least one of said first and second movable stoppers disposed adjacent said first end; and
   an injection nozzle disposed adjacent said second end and further including a receptacle and at least one injection duct, said receptacle containing a cavity configured to receive the first movable stopper wherein said cavity has a height equal to or greater than that of the first movable stopper.

8. The needleless injection device as claimed in claim 7, wherein one of the first and second movable stoppers is upstream and the other of the first and second movable stoppers is downstream.

9. The needleless injection device as claimed in claim 7, wherein said reservoir is adjacent said at least one injection duct when the first movable stopper is received in said cavity.

10. The needleless injection device as claimed in claim 8, wherein the downstream movable stopper is received in said cavity and said liquid active principle is transmitted from said reservoir to an inlet attached to said at least one injection duct.

11. The needleless injection device as claimed in claim 7, wherein the height of the cavity in millimeters is between a minimum height and a maximum height respectively defined by the following equations:

• minimum height=3

• maximum height=$15 \times \exp(-(V/9)^2)+10$ where V is a speed of an initial increase in a pressure profile expressed in bars per microsecond;

a ratio between a length of said at least one injection duct and the height of the cavity is between 1 and 2.

12. The needleless injection device as claimed in claim 11, wherein the minimum height of the cavity in millimeters is defined by the following equation:

• minimum height=$12 \times \exp(-(V/18)^2)+4$.

13. The needleless injection device as claimed claim 11, wherein the maximum height of the cavity in millimeters is defined by the following equation:

• maximum height=$14 \times \exp(-(V/9)^2)+9$.

14. A needleless injection device comprising:
a body having a first end and a second end;
an energy source connected to said first end;
a reservoir disposed within said body and having a downstream movable stopper and an upstream movable stopper with a liquid active principle contained therebetween wherein a movement of at least one of said stoppers is generated by said energy source; and
an injection nozzle disposed within the second end and adjacent said downstream movable stopper, said injection nozzle including a receptacle and at least one injection duct wherein said receptacle contains a cavity configured to receive said downstream movable stopper such that the liquid active principle is transmitted from said reservoir towards said at least one injection duct.

15. The needleless injection device as claimed in claim 14, wherein the cavity has a height and said height in millimeters is between a minimum height and a maximum height respectively defined by the following equations:

• minimum height=3

• maximum height=$15 \times \exp(-(V/9)^2)+10$ where V is a speed of an initial increase in a pressure profile expressed in bars per microsecond;

a ratio between a length of said at least one injection duct and the height of the cavity is between 1 and 2.

16. The needleless injection device as claimed in claim 15, wherein the minimum height of the cavity in millimeters is defined by the following equation:

• minimum height=$12 \times \exp(-(V/18)^2)+4$.

17. The needleless injection device as claimed claim 15, wherein the maximum height of the cavity in millimeters is defined by the following equation:

• maximum height=$14 \times \exp(-(V/9)^2)+9$.

* * * * *